United States Patent
Sahbari et al.

(10) Patent No.: US 6,235,935 B1
(45) Date of Patent: May 22, 2001

(54) METHOD OF MANUFACTURING HIGH PURITY OXIMES FROM AQUEOUS HYDROXYLAMINE AND KETONES

(75) Inventors: Javad J. Sahbari; Jin Wang Russell, both of Sunnyvale, CA (US)

(73) Assignee: Silicon Valley Chemlabs, Inc., Sunnyvale, CA (US)

( * ) Notice: Subject to any disclaimer, the term of this patent is extended or adjusted under 35 U.S.C. 154(b) by 0 days.

(21) Appl. No.: 09/199,399

(22) Filed: Nov. 24, 1998

(51) Int. Cl.[7] .................................................. C07C 249/00
(52) U.S. Cl. .............................................................. 564/259
(58) Field of Search ................................................ 564/259

(56) References Cited

U.S. PATENT DOCUMENTS

| | | |
|---|---|---|
| 3,429,920 | 2/1969 | de Rooij . |
| 3,941,840 | 3/1976 | Rotaru . |
| 4,128,579 | 12/1978 | Berthold . |
| 4,929,756 | 5/1990 | Kuma . |
| 5,117,060 | 5/1992 | Witzeman . |
| 5,254,734 | 10/1993 | Kanda et al. . |
| 5,300,689 | 4/1994 | Krbechek et al. . |
| 5,488,161 | 1/1996 | Krbechek . |

OTHER PUBLICATIONS

C.A. 127:81069 (1997).*

* cited by examiner

*Primary Examiner*—Paul J. Killos
(74) *Attorney, Agent, or Firm*—David H. Jaffer; Pillsbury Winthrop LLP

(57) ABSTRACT

High purity oximes are prepared from aqueous hydroxylamine and ketones reacted at ambient temperature without addition of impurities such as salts or acids.

7 Claims, No Drawings

METHOD OF MANUFACTURING HIGH PURITY OXIMES FROM AQUEOUS HYDROXYLAMINE AND KETONES

BACKGROUND OF THE INVENTION

1. Field of the Invention

This invention relates to an improved method for making oximes. The method uses aqueous hydroxylamine and a ketone.

2. Brief Description of the Prior Art

Oximes of general formula $R_1 R_2 C=NOH$, where $R_1$ and $R_2$ are alkyl or an alkoxy groups, are used extensively as intermediates in manufacturing of other products.

U.S. Pat. No. 3,429,920 describes a method for producing oximes from ketones by using a hydroxylamine salt in a buffered solution of a weak acid and a salt of the weak acid. This method is complicated and time consuming, and adds impurities.

SUMMARY OF THE INVENTION

The present invention provides a simple, convenient method for preparing oximes, using an aqueous hydroxylamine and ketone solution.

This method has several advantages over the traditional methods: (a) it is fast and spontaneous therefore giving a high production yield; and (b) it does not need a long and difficult process or costly apparatus.

Briefly, in the preferred embodiment, a high purity oxime such as acetone oxime, $CH_3—C(CH_3)=NOH$, can be prepared using free hydroxylamine base and a ketone. In some cases, the reaction proceeds spontaneously, and with other reactants the media must be acidified in order to initiate reaction. A 50% by weight aqueous solution of hydroxylamine base is mixed with high purity ketone. The crystalline oxime material can be filtered and recrystallized using an inert fluorocarbon solvent for further purification.

DESCRIPTION OF THE PREFERRED EMBODIMENT

The present invention is a method for making high purity oximes using an aqueous hydroxylamine solution and ketones. The examples given below use acetone, acetyl acetone (2, 4pentanedione), and cyclohexanone to yield acetone oxime, acetyl acetone dioxime, and cyclohexanone oxime, but the method has also been used with methyl ethyl ketone, methyl isopropyl ketone, methyl isobutyl ketone, and cylcopentanone to yield the corresponding oximes. Of these examples, only acetone requires acidification, as discussed below. When acidification is required, preferably a high purity organic acid such as formic, acetic, citric, or oxalic acid is used. Inorganic acids, such as hydrochloric, sulfuric, nitric, or phosphoric acids, may be used but may lead to unwanted ionic or inorganic contaminants. Those skilled in the art will recognize that analogous ketones may be used to create other oximes.

EXAMPLE 1

50 ml of high purity acetone was added to 100 ml of high purity 50% hydroxylamine/50% water (percentages by weight), and stirred with a magnetic stirrer. The mixture was left to reach equilibrium by sitting a few hours to reach ambient temperature (approximately 25° C.). 50 ml of 98% formic acid in water was then added to the mixture to yield a pH of 6.0–6.2, and mixed to reach equilibrium. Crystalline acetone oxime separated. The mixture was stirred for 24 hours at ambient temperature to complete formation of crystals and filtered the next day. The acetone oxime was purified as follows: The crystals were filtered and then dissolved in a non-polar solvent (perfluorocyclohexane) by heating, and cooled overnight at ambient temperature for recrystallization. The crystalline material was then filtered and washed with perfluorocyclohexane. The melting point was 61° C.–63° C., and the yield 85%–90%. The product was analyzed by FT-IR, GC/MS, NMR, and other methods to confirm the molecular structure. The crystal structure was determined by x-ray methods.

The product is believed to be formed by the following reaction:

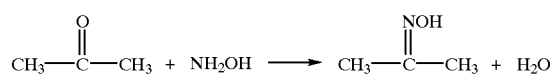

Table 1 illustrates yields when different acids are substituted for formic acid. The acids were added to achieve a pH of 6.0 to 6.2, and otherwise the reaction conditions were the same as in Example 1.

TABLE 1

Yield and Melting Point Results When Acetone Oxime Prepared With Different Acids

| Acid | Yield | Melting Point (° C.) |
| --- | --- | --- |
| $H_2SO_4$ | 87.5% | 62–64 |
| $HNO_3$ | 83.5% | 62–64 |
| HCl | 76.7% | 62–63 |
| Acetic | 78.6% | 62–63 |
| Citric | 78.6% | 62–64 |

EXAMPLE 2

50 ml of high purity acetyl acetone was gradually added to 100 ml of high purity 50% hydroxylamine/50%. water in a glass beaker, and stirred with a magnetic stirrer overnight at ambient temperature. Crystalline acetyl acetone dioxime separated. The crystals were filtered and purified as in Example 1. 54 g of crystals were obtained, melting point 140–144° C., yield 83%. Formation is believed to occur as follows:

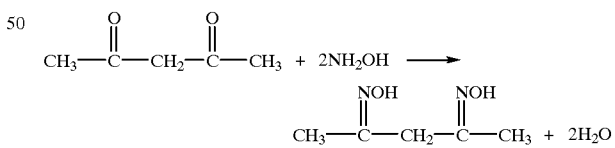

EXAMPLE 3

50 ml of high purity cyclohexanone was gradually added to 100 ml of high purity 50% hydroxylamine/50% water in a glass beaker, and stirred with a magnetic stirrer overnight at ambient temperature. Crystalline cyclohexanone oxime separated. The crystals were filtered and purified as in Example 1. 55 g of crystals were obtained, melting point 86–900° C., yield 95%. Formation is believed to occur as follows:

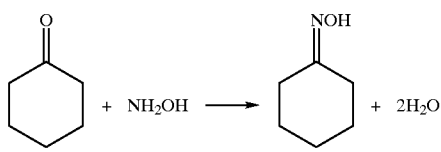

The above examples illustrate synthesis of oximes at close to 100% yields, without addition of contaminating salts or acids.

Although the present invention has been described above in terms of a specific embodiment, it is anticipated that alterations and modifications thereof will no doubt become apparent to those skilled in the art. It is therefore intended that the following claims be interpreted as covering all such alterations and modifications as fall within the true spirit and scope of the invention.

What is claimed is:

1. A method for making an oxime comprising mixing an aqueous hydroxylamine solution with a ketone, wherein the solution is essentially free of added catalysts, ammonia, and hydrogen peroxide.

2. The method of claim 1 wherein the aqueous hydroxylamine solution has from 20% to 80% by weight hydroxylamine.

3. The method of claim 2, wherein the ketone is chosen from the group consisting of methyl ethyl ketone, acetyl acetone, cyclohexanone, methyl isopropyl ketone, methyl isobutyl ketone, and cyclopentanone.

4. A method for making an oxime comprising the steps of:
   (a) adding a ketone selected from the group consisting of methyl ethyl ketone, acetyl acetone, cyclohexanone, methyl isopropyl ketone, methyl isobutyl ketone, and cyclopentanone to an aqueous hydroxylamine solution having from 30% to 70% by weight hydroxylamine, wherein the solution is essentially free of added catalysts, ammonia, and hydrogen peroxide;
   (b) mixing the ketone and the aqueous hydroxylamine solution to cause formation of the oxime; and
   (c) separating the oxime.

5. A method for making acetone oxime comprising the steps of:
   (a) mixing an aqueous hydroxylamine solution having from 20% to 80% by weight hydroxylamine with acetone, wherein the solution is essentially free of added catalysts, ammonia, and hydrogen peroxide; and
   (b) adding an acid to the mixture to cause formation of the oxime.

6. The method of claim 5, wherein the acid is chosen from the group consisting of formic, acetic, citric and oxalic acids.

7. The method of claim 5, wherein the acid is an inorganic acid chosen from the group consisting of hydrochloric, sulfuric, nitric and phosphoric acids.

* * * * *